United States Patent
Gallou et al.

(10) Patent No.: US 11,235,316 B2
(45) Date of Patent: Feb. 1, 2022

(54) CATALYSTS FOR CHEMICAL REACTIONS IN A WATER-SURFACTANT MIXTURE

(71) Applicant: Novartis AG, Basel (CH)

(72) Inventors: Fabrice Gallou, Basel (CH); Pengfei Guo, Jiangsu (CN); Jianguang Zhou, Jiangsu (CN); Michael Parmentier, Basel (CH)

(73) Assignee: Novartis AG, Basel (CH)

( * ) Notice: Subject to any disclaimer, the term of this patent is extended or adjusted under 35 U.S.C. 154(b) by 23 days.

(21) Appl. No.: 16/316,709

(22) PCT Filed: Jul. 10, 2017

(86) PCT No.: PCT/IB2017/054139
§ 371 (c)(1),
(2) Date: Jan. 10, 2019

(87) PCT Pub. No.: WO2018/011696
PCT Pub. Date: Jan. 18, 2018

(65) Prior Publication Data
US 2019/0308180 A1    Oct. 10, 2019

(30) Foreign Application Priority Data
Jul. 13, 2016  (WO) ................ PCT/CN2016/089854

(51) Int. Cl.
*C07C 211/04*   (2006.01)
*B01J 31/22*    (2006.01)
(Continued)

(52) U.S. Cl.
CPC .......... *B01J 31/2273* (2013.01); *B01J 13/00* (2013.01); *B01J 31/0204* (2013.01); *B01J 31/0215* (2013.01); *B01J 31/0239* (2013.01); *B01J 31/0244* (2013.01); *B01J 31/0271* (2013.01); *B01J 31/1815* (2013.01); *B01J 31/2419* (2013.01); *B01J 31/2438* (2013.01); *C08L 71/00* (2013.01); *B01J 2231/14* (2013.01); *B01J 2231/40* (2013.01); *B01J 2231/4211* (2013.01);
(Continued)

(58) Field of Classification Search
None
See application file for complete search history.

(56) References Cited

U.S. PATENT DOCUMENTS

| | | | |
|---|---|---|---|
| 2004/0147740 A1* | 7/2004 | Hirano | C07D 251/46 544/112 |
| 2007/0135632 A1 | 6/2007 | Kunishima | |

FOREIGN PATENT DOCUMENTS

| | | |
|---|---|---|
| JP | 2016098194 A | 5/2016 |
| WO | 2005/075442 A1 | 8/2005 |

OTHER PUBLICATIONS

Hojo et al. (Protein & Peptide Letters, 2006, 13, 189-192 (Year: 2006).*

(Continued)

*Primary Examiner* — Yun Qian
(74) *Attorney, Agent, or Firm* — Francine F. Li

(57) ABSTRACT

The present invention is directed to reaction mixtures comprising a water-surfactant mixture, wherein the catalyst comprises a compound with solubilizing groups. This technology improves the solubility of the reaction components in the water-surfactant mixture and thereby, greatly increases the productivity and selectivity of the chemical reaction.

18 Claims, 1 Drawing Sheet

(51) Int. Cl.
  *B01J 13/00* (2006.01)
  *B01J 31/02* (2006.01)
  *B01J 31/24* (2006.01)
  *C08L 71/00* (2006.01)
  *B01J 31/18* (2006.01)
  *C07C 231/02* (2006.01)
  *C07C 233/73* (2006.01)

(52) U.S. Cl.
  CPC .. *B01J 2231/4266* (2013.01); *B01J 2531/004* (2013.01); *B01J 2531/005* (2013.01); *B01J 2531/821* (2013.01); *B01J 2531/822* (2013.01); *B01J 2531/824* (2013.01); *B01J 2531/847* (2013.01); *B01J 2531/96* (2013.01); *B01J 2531/985* (2013.01); *C07C 231/02* (2013.01); *C07C 233/73* (2013.01)

(56) References Cited

OTHER PUBLICATIONS

Lindstroem U M, "Stereoselective Organic Reactions in Water", Chemical Rev, American Chemical Society, vol. 102, Jan. 1, 2002 (Jan. 1, 2002), pp. 2751-2772.

Liu et al., "Toward green catalytic synthesis—Transition metal-catalyzed reactions in non-conventional media", Journal of Molecular Catalysis A: Chemical, Elsevier, Amsterdam, NL, vol. 270, No. 1-2, May 7, 2007 (May 7, 2007), pp. 1-43.

Lipshutz et al., "PQS-2: ring-closing and cross-metathesis reactions on lipophilic substrates; in water only at room temperature, with in-flask catalyst recycling", Tetrahedron, Elsevier Science Publishers, Amsterdam, NL, vol. 66, No. 5, Jan. 30, 2010 (Jan. 30, 2010), pp. 1057-1063.

Munetaka Kunishima et al., "Substrate-Selective Dehydrocondensation at the Interface of Micelles and Emulsions of Common Surfactants", Angewandte Chemie International Edition, vol. 51, No. 9, Jan. 20, 2012 (Jan. 20, 2012), pp. 2080-2083.

Munetaka Kunishima et al., "Unusual Rate Enhancement of Bimolecular Dehydrocondensation To Form Amides at the Interface of Micelles of Fatty Acid Saits", Angewandte Chemie International Edition, vol. 44, No. 44, Oct. 17, 2005 (Oct. 17, 2005), pp. 7254-7257.

Gallou et al., "A General and Practical Alternative to Polar Aprotic Solvents Exemplified on an Amide Bond Formation", Organic Process Research and Development, vol. 20, No. 7, Jun. 22, 2016 (Jun. 22, 2016), pp. 1388-1391.

\* cited by examiner

A
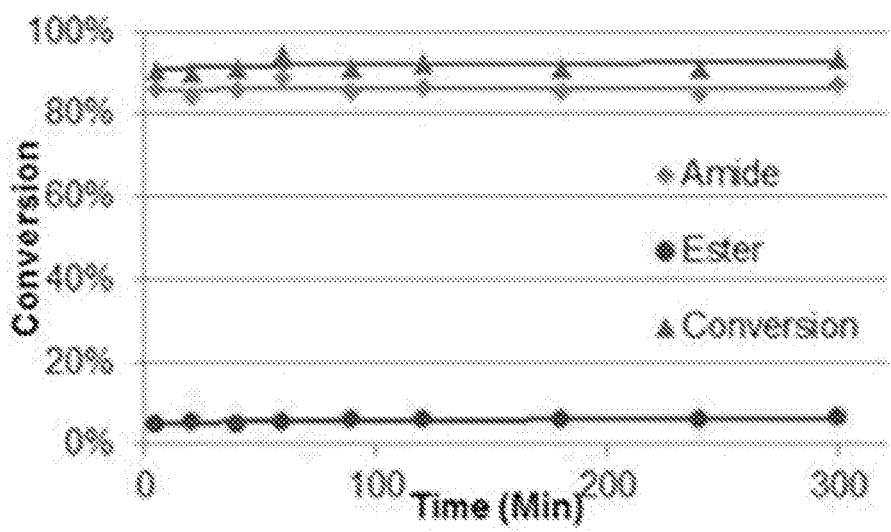
Triazine 6c
B
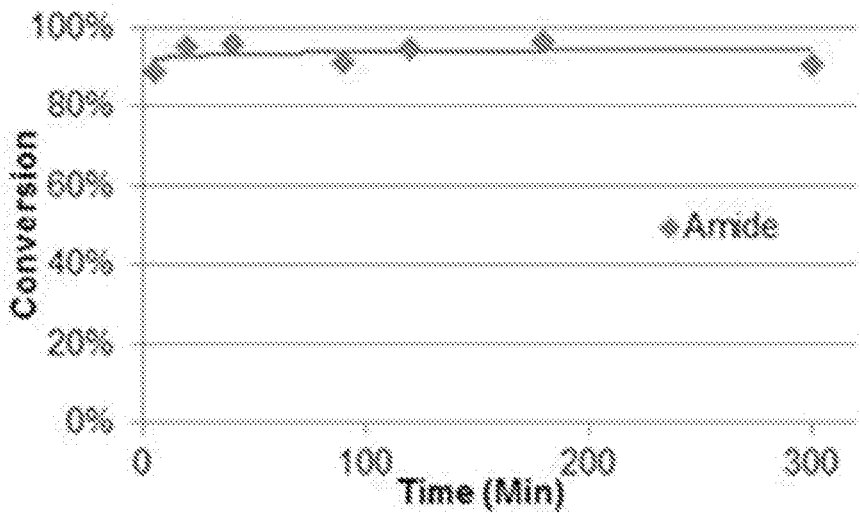
Triazine 6h

CATALYSTS FOR CHEMICAL REACTIONS IN A WATER-SURFACTANT MIXTURE

FIELD OF THE INVENTION

The present invention is directed to improvements of chemical reactions using surfactant-water reaction media. Solubility of the reaction components is increased by catalyst compounds modified with solubilizing groups. Thereby, yield and selectivity of the chemical reaction is greatly enhanced. Hence, the present invention pertains to chemical reaction mixtures comprising respectively modified catalyst compounds and a surfactant-water mixture.

BACKGROUND OF THE INVENTION

The identification of sustainable harmless solvent to be used for general purposes has been an area of focus by many chemistry groups globally in the last few decades. It became all the more important as not only the well-known ozone-depleting chlorinated solvents were flagged many years ago, but also when the reprotoxicity of such frequently used polar aprotic solvents as DMF, DMAC or NMP was made visible. To tackle this particular topic, a variety of more or less general strategies were followed by multiple groups around the world, developing neoteric solvents for example, which will have given rise to such solvents as the bio-based cyrene, or such ethers as CPME or the more powerful MeTHF, other harmless derivatives of problematic solvents developed directly by chemical producers, ionic liquids, or more sophisticated systems utilizing compressed gases or phase-transfer catalysis, switchable solvents, and fluorous systems. While punctual success stories can be found and have proven tremendous benefits at times, the generality is however lagging behind. This unfortunately did not yet lead to the required dramatic change in mindset. For example, time-critical experimentations continue relying on the most established undesirable DMF or NMP for example. This is all the more critical and relevant in the pharmaceutical industry where the physical properties of the target compounds routinely display limited solubility.

One approach towards the replacement of undesirable polar aprotic solvents was developed by Professor Lipshutz, disclosing his latest application on the benign-by-design surfactant chemistry.

However, there is a need in the art to improve the chemical reactions in the surfactant solvent systems to increase productivity and reduce unwanted side products.

SUMMARY OF THE INVENTION

The present invention is based on the findings that in reaction mixtures using a surfactant-water mixture as reaction medium, solubilizing groups attached to the catalyst compounds greatly enhance solubilization of the reaction partners. This has a huge impact on the productivity as well as the selectivity of the reaction. Especially alkyl groups and poly(ethylene glycol) groups of medium length show highly promising results when attached to coupling reagents or complexing ligands of metal catalysts.

In a first aspect, the present invention provides a reaction mixture comprising one or more reactants, a catalyst and a surfactant-water mixture, wherein the catalyst is (a) a coupling reagent comprising one or more solubilizing groups; or (b) a metal ion in complex with a ligand comprising one or more solubilizing groups; wherein the solubilizing group comprises a C5-50 alkyl group or a poly(alkylene glycol) group with 2 to 20 repeating units.

In a second aspect, the present invention provides a method of performing a chemical reaction, comprising the steps of
(a) providing a reaction mixture according to the first aspect of the invention, and
(b) allowing the chemical reaction to proceed.

In a third aspect, the present invention provides a method of increasing the yield of a chemical reaction, and/or decreasing the amount of side products produced in a chemical reaction, wherein the chemical reaction is performed in a surfactant-water mixture, comprising the steps of
(a) providing a reaction mixture comprising one or more reactants, a catalyst, and a surfactant-water mixture, wherein the catalyst is a coupling reagent comprising one or more solubilizing groups, or a metal ion in complex with a ligand comprising one or more solubilizing groups; wherein the solubilizing group comprises a $C_{5-50}$ alkyl group or a poly(alkylene glycol) group with 2 to 20 repeating units; and
(b) allowing the chemical reaction to proceed.

The above aspects can be combined. Other objects, features, advantages and aspects of the present invention will become apparent to those skilled in the art from the following description and appended claims. It should be understood, however, that the following description, appended claims, and specific examples, which indicate preferred embodiments of the application, are given by way of illustration only. Various changes and modifications within the spirit and scope of the disclosed invention will become readily apparent to those skilled in the art from reading the following.

DETAILED DESCRIPTION OF THE INVENTION

The present invention provides, in a first aspect, a reaction mixture comprising one or more reactants, a catalyst and a surfactant-water mixture, wherein the catalyst is (a) a coupling reagent comprising one or more solubilizing groups; or (b) a metal ion in complex with a ligand comprising one or more solubilizing groups; wherein the solubilizing group comprises a C5-50 alkyl group or a poly(alkylene glycol) group with 2 to 20 repeating units.

The inventive technology is suitable for all chemical reactions which can be performed in a medium comprising a surfactant-water mixture. It can in particular be used in organic chemistry, for example with at least partly hydrophobic compounds. Exemplary suitable chemical reactions include chemical reactions selected from the group consisting of cross-coupling reactions such as Suzuki cross-coupling, Suzuki-Miyaura cross-coupling, Sonogashira cross-coupling, Heck cross-coupling, Buchwald-Hartwig cross-coupling, Negishi cross-coupling, Stille cross-coupling, Miyaura borylation, Hiyama cross-couplings, Chan-Ma cross-coupling, and olefin metathesis; copper-mediated cross-couplings, nickel-mediated cross-couplings, nucleophilic substitutions such as nucleophilic aromatic substitution ($S_NAr$); electrophilic halogenation, aromatic and heteroaromatic halogenation; biocatalytic transformations; amidation; oxidation; reduction such as reduction of nitro groups, oxime groups, azide groups, nitrile groups and amide groups; nitrile and imine hydrolysis; hydrogenation and debenzylation. In certain embodiments, the chemical reaction is an amidation. In these embodiments, the catalyst preferably is a coupling reagent. The reactants and the catalyst present in the reaction mixture are suitable for the specific chemical reaction. In particular, the reactants and the catalyst are specifically chosen so that the chemical reaction can be performed.

The surfactant in the surfactant-water mixture can be any surfactant. In particular, the surfactant should not interfere with the chemical reaction. In certain embodiments, the surfactant is a non-ionic surfactant. The surfactant generally is amphiphilic and comprises a hydrophilic part and a hydrophobic part. In specific embodiments, the surfactant is able to form micelles in the surfactant-water mixture.

In certain embodiments, the hydrophilic part of the surfactant comprises a polyalkylene glycol moiety, especially a polyethylene glycol moiety or a polypropylene glycol moiety. The polyalkylene moiety, especially the polyethylene glycol moiety, may have an average molecular weight in the range of about 100 to about 10,000 g/mol, especially in the range of about 300 to about 3,000 g/mol, in particular in the range of about 400 to about 2,000 g/mol. Certain examples of surfactants comprising a polyalkylene glycol moiety include tocopherol polyethylene glycol succinates (TPGS), in particular DL-α-tocopherol polyethylene glycol succinates such as TPGS-750-M, TPGS-1000, TPGS-1500, TPGS-400, TPGS-1100-M, TPGS-2000, TPGS-860-oleate, TPGS-PEG-PPG-PEG-1100 and TPGS-PPG-PEG-70-butyl, and DL-α-tocopherol polypropylene glycol succinates such as TPPG-1000 and TPPG-1000-butyl; Triton X-100; polyethylene glycol alkyl ethers such as Brij surfactants, in particular Brij 30, Brij 35, Brij 52, Brij 56, Brij 58, Brij 72, Brij 76, Brij 78, Brij 92, Brij 96, Brij 98, Cremophor A6, Cremophor A25 and Thesit; polyethylene glycol esters such as polyethylene glycol (15)-hydroxystearate (Solutol HS 15); polyethylene glycol sorbitan fatty acid esters, also known as polysorbates or Tween, such as polysorbate 20, polysorbate 21, polysorbate 40, polysorbate 60, polysorbate 61, polysorbate 65, polysorbate 80, polysorbate 81, polysorbate 85 and polysorbate 120; cholesteryl PEG succinates such as holesteryl PEG1000 succinate; (deoxy) cholic PEG such as colic PEG1000 and deoxy-cholic PEG1000; chromanol polyethylene glycol succinates such as Chrom-400 and Chrom-1000; b-sitosterol methoxyethyleneglycol succinate (Nok); and other derivatives of PEG such as C4-azo-PEG. In specific embodiments, the surfactant is a DL-α-tocopherol polyethylene glycol succinate, in particular TPGS-750-M.

Furthermore, also other surfactants can be used, including, for example, cetyltrimethylammonium bromide (CTAB); phase transfer surfactants (PTS) such as sodium deoxycholate; polyoxyethanyl ubiquinol sebacate (PQS) and functionalized PQS; and octanoic acid and other long alkyl chain acids, in particular C6-C20 alkyl chain acids.

The concentration of the surfactant in the surfactant-water mixture in particular is in the range of 0.1 to 10% (w/w). In certain embodiments, the concentration of the surfactant in the surfactant-water mixture is in the range of 0.5 to 5% (w/w), especially in the range of 0.8 to 4% (w/w), 1 to 3% (w/w) or 1.5 to 2.5% (w/w), such as about 2% (w/w). In specific embodiments, the concentration of the surfactant in the surfactant-water mixture is above its critical micellar concentration.

The catalyst in the reaction mixture is a coupling reagent comprising one or more solubilizing groups or a metal ion in complex with a ligand comprising one or more solubilizing groups. Suitable catalysts and ligands are known in the art and can readily be selected by a person skilled in the art. The coupling reagent or metal ion in complex with a ligand is not restricted to specific compounds as long as it is suitable for catalyzing the chemical reaction of the reactants into the desired product. Hence, the choice of the catalyst depends on the type of chemical reaction to be performed in the reaction mixture.

In embodiments wherein the catalyst is a coupling reagent, it is in particular a coupling reagent for amide formation. Especially, it may be selected from the group consisting of (i) coupling reagents for coupling via activated ester such as carbodiimides, in particular N,N'-dicyclohexylcarbodiimide, N,N'-diisopropylcarbodiimide and 1-ethyl-3-(3'-dimethylaminopropyl)-carbodiimide, phosphonium salts, in particular (benzotriazol-1-yloxy)-tris(dimethylamino)-phosphonium hexafluorophosphate and (benzotriazol-1-yloxy)-tris(pyrrolidine)-phosphonium hexafluorophosphate, guanidinium and uronium salts, in particular N,N,N',N'-tetramethyl-O-(1H-benzotriazol-1-yl)uronium hexafluorophosphate, N-[(dimethylamino)-1H-1,2,3-triazolo[4,5-b]pyridin-1-yl-methylene]-N-methylmethan-aminium hexafluorophosphate N-oxide, N-[(1H-benzotriazol-1-yl)(dimethylamino)methylene]-N-methylmethanaminium tetrafluoroborate N-oxide, 2-(2-oxo-1 (2H)-pyridyl-1,1,3,3-tetramethyluronium tetrafluoroborate and O-[(cyano (ethoxycarbonyl)-methyleneamino]-N,N,N',N'-tetramethyluronium tetrafluoroborate, and triazine compounds, in particular cyanuric chloride, 2-chloro-4,6-dimethoxy-1,3,5-triazine and 4-(4,6-dimethoxy-1,3,5-triazin-2-yl)-4-methylmorpholinium chloride; and (ii) coupling reagents for coupling via boron species such as boric acid and 3-nitrophenylboronic acid.

In certain embodiments, the coupling reagent is a 1,3,5-triazine derivative. The 1,3,5-triazine derivative may comprise a quaternary amine which in particular may be attached to the 2-position of the triazine ring. The quaternary amine may be formed by a trialkylamino group such as a trimethylamino group, or an N-alkyl-N-morpholino group such as an N-methyl-N-morpholino group, attached to the triazine ring. Furthermore, the 1,3,5-triazine derivative may be substituted with methyl, ethyl, propyl, methoxy, ethoxy and/or propoxy, in particular at the 4- and/or the 6-position of the triazine ring. In certain embodiments, the one or more solubilizing groups are attached to the quaternary amine and/or the 4- and/or 6-position of the triazine ring.

In specific embodiments, the coupling reagent has the general formula (I)

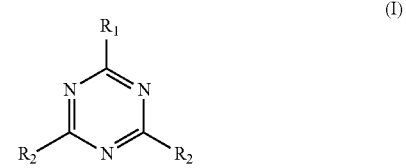

wherein
$R_1$ is $-N^+(R_3)_3$;
each of $R_2$ is independently C1-5 alkoxy, C1-5 alkyl, hydroxy, amino optionally substituted with one or two C1-5 alkyl, or $-N^+(R_3)_3$, wherein the C1-5 alkyl or alkoxy group is optionally substituted with one or two groups selected from hydroxy, amino, methoxy and ethoxy, and/or wherein optionally one or two carbon atoms are replaced by oxygen, sulfur or nitrogen;
each of $R_3$ is independently C1-5 alkyl optionally substituted with one or two groups selected from hydroxy, amino, methoxy and ethoxy, and/or wherein optionally one or two carbon atoms are replaced by oxygen, sulfur or nitrogen, and wherein two $R_3$ groups may optionally form a C4-7 heterocycle with the nitrogen atom to which they are attached, wherein optionally one or two carbon atoms are replaced by oxygen, sulfur or nitrogen;

and wherein at least one of $R_2$ and/or $R_3$ is replaced by a solubilizing group.

In certain embodiments, $R_1$ is —$N_+(R_3)_3$, wherein all of $R_3$ are methyl. In these embodiments, preferably one of the $R_3$ groups is replaced by a solubilizing group and in particular both of $R_2$ are methoxy. In other embodiments, $R_1$ is —$N^+(R_3)_3$, wherein one of $R_3$ is methyl and the other two of $R_3$ together with the nitrogen form a morpholine ring. In these embodiments, preferably at least one and in particular both of the $R_2$ groups are replaced by a solubilizing group. In these embodiments, the $R_2$ group not replaced by a solubilizing group in particular is methoxy or N-methylmorpholin-4-yl.

In certain embodiments, charged coupling reagents further comprise a counter ion such as chloride, bromide, iodide, hexafluorophosphate or tetrafluoroborate.

In certain embodiments the catalyst is an amide coupling reagent such as a triazine compound. In these embodiments, the reaction mixture is in particular used for an amidation reaction. In these embodiments, the reaction mixture preferably comprises a carboxylic acid and an amine as reactants. In other embodiments, the triazine compound is used as a coupling reagent in a selective reduction or a cross-coupling reaction with an organo-metallic compound.

In embodiments wherein the catalyst is a metal ion in complex with a ligand, the metal ion may be selected from the group consisting of copper ion, ruthenium ion, rhodium ion, palladium ion, nickel ion, zinc ion, gold ion, manganese ion, iron ion and cobalt ion. The ligand may be any ligand suitable for complexing the metal ion. It may be selected from the group consisting of biphenyl compounds; carbene compounds such as N-heterocyclic carbenes, in particular 1,3-bis(2,4,6-trimethylphenyl)imidazol-2-ylidene; bi-N-heteroaromatic compounds such as bipyridine compounds.

In specific embodiments, the ligand is a biphenyl compound having the general formula (II)

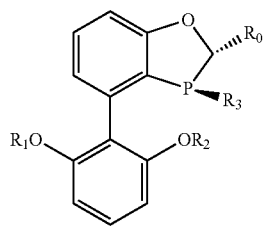

(II)

wherein $R_1$, $R_2$ and $R_3$ are independently of each other hydrogen or C1-5 alkyl optionally substituted with one or two groups selected from hydroxy, amino, methoxy and ethoxy, and/or wherein optionally one or two carbon atoms are replaced by oxygen, sulfur or nitrogen;

$R_0$ is H, or C1-5 alkyl, in particular methyl, or $CH_2$—Ar, wherein Ar is a phenyl or benzyl optionally substituted with 1, 2, 3, 4 or 5 $R_4$, and wherein the C1-5 alkyl group is optionally substituted with one or two groups selected from hydroxy, amino, methoxy and ethoxy, and/or wherein optionally one or two carbon atoms are replaced by oxygen, sulfur or nitrogen;

each $R_4$ is independently of each other C1-5 alkoxy, C1-5 alkyl, poly(ethylene glycol) with 2, 3 or 4 repeating units, poly(propylene glycol) with 2, 3 or 4 repeating units, hydroxy or amino optionally substituted with one or two C1-5 alkyl, wherein the C1-5 alkyl or alkoxy group is optionally substituted with one, two or three groups selected from hydroxy, halogen, amino, methoxy and ethoxy, and/or wherein optionally one or two carbon atoms are replaced by oxygen, sulfur or nitrogen, and wherein the poly(ethylene glycol) and poly(propylene glycol) is optionally substituted with methyl, ethyl or propyl at the terminal oxygen;

and wherein at least one of $R_0$, $R_1$, $R_2$ and $R_4$, preferably at least one of $R_1$ and $R_2$, especially both of $R_1$ and $R_2$, is replaced by a solubilizing group.

In certain embodiments, Ar is phenyl substituted with electron- or electron-withdrawing groups such as isopropyl or trifluoromethyl groups. For example, Ar may be 2,4,6-tris-isopropyl phenyl or 3,5-bis-trifluoromethyl phenyl. Furthermore, $R_3$ preferably is tertiary butyl. $R_1$ and $R_2$, if not replaced by a solubilizing group, preferably are methyl.

In further embodiments, the ligand is an N-heterocyclic carbene compound having the general formula (III)

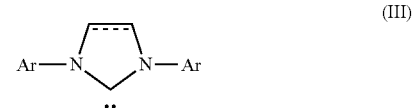

(III)

wherein each Ar is independently from each other a phenyl optionally substituted with 1, 2, 3, 4 or 5 $R_1$;

each $R_1$ is independently of each other C1-5 alkoxy, C1-5 alkyl, poly(ethylene glycol) with 2, 3 or 4 repeating units, poly(propylene glycol) with 2, 3 or 4 repeating units, hydroxy or amino optionally substituted with one or two C1-5 alkyl, wherein the C1-5 alkyl or alkoxy group is optionally substituted with one or two groups selected from hydroxy, amino, methoxy and ethoxy, and/or wherein optionally one or two carbon atoms are replaced by oxygen, sulfur or nitrogen, and wherein the poly(ethylene glycol) and poly(propylene glycol) is optionally substituted with methyl, ethyl or propyl at the terminal oxygen;

and wherein at least one of the $R_1$ groups, preferably one $R_1$ on each Ar group is replaced by a solubilizing group.

In specific embodiments, each Ar is phenyl substituted with three $R_1$ in 2-, 4- and 6-position, wherein each $R_1$ is methyl, and wherein at least one $R_1$, especially one $R_1$ on each Ar, is replaced by a solubilizing group.

In further embodiments, the ligand is a bipyridine compound having the general formula (IV)

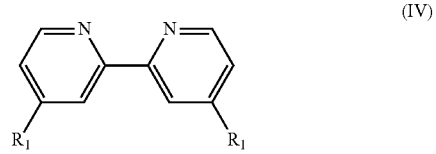

(IV)

wherein each $R_1$ is independently of each other C1-5 alkoxy, C1-5 alkyl, poly(ethylene glycol) with 2, 3 or 4 repeating units, poly(propylene glycol) with 2, 3 or 4 repeating units, hydroxy or amino optionally substituted with one or two C1-5 alkyl, wherein the C1-5 alkyl or alkoxy group is optionally substituted with one or two groups selected from hydroxy, amino, methoxy and ethoxy, and/or wherein optionally one or two carbon atoms are replaced by oxygen, sulfur or nitrogen, and wherein the poly(ethylene glycol) and poly(propylene glycol) is optionally substituted with methyl, ethyl or propyl at the terminal oxygen;

and wherein at least one of the $R_1$ groups, preferably both $R_1$ groups are replaced by a solubilizing group.

In specific embodiments, one $R_1$ is methoxy and the other is replaced by a solubilizing group, or both of $R_1$ are replaced by a solubilizing group.

The concentration of the catalyst in the reaction mixture is selected so that it is able to catalyze the desired chemical reaction. In embodiments wherein the catalyst is a metal ion in complex with a ligand, suitable catalyst concentrations are for example 0.1 to 25 mol %, especially 1 to 20 mol %, 3 to 15 mol % or 5 to 10 mol %, with respect to the molar amount of one or more of the reactants. In embodiments wherein the catalyst is a coupling reagent, the catalyst is present in stoichiometric amounts. In particular, the concentration of the coupling reagent is 75 to 250 mol %, especially 90 to 200 mol %, 100 to 150 mol % or 110 to 130 mol %, with respect to the molar amount of one or more of the reactants.

The coupling reagent or ligand comprises one or more solubilizing groups. That is, the coupling reagent or ligand comprises one, two, three, four, five or more solubilizing groups. In one embodiment, the coupling reagent or ligand comprises one solubilizing group. In another preferred embodiment, the coupling reagent or ligand comprises two solubilizing groups. In embodiments wherein the coupling reagent or ligand comprises more than one solubilizing group, the solubilizing groups may be different or the same, and in particular are the same. Each of the solubilizing groups comprises a $C_{5-50}$ alkyl group or a poly(alkylene glycol) group with 2 to 20 repeating units. The solubilizing groups are attached to the remaining part of the coupling reagent or ligand via a covalent bond or a functional group such as an ether group, an ester group, an amine group, an amide group, a thioether group, a thioester group, or a thioamide group.

In specific embodiments, the solubilizing group comprises a $C_{5-50}$ alkyl group. The alkyl group may be linear or branched or cyclic and in particular is linear. The alkyl group has 5 to 50 carbon atoms, in particular 5 to 25 carbon atoms, preferably 6 to 20 carbon atoms, 7 to 18 carbon atoms, 8 to 15 carbon atoms or 10 to 14 carbon atoms, especially about 12 carbon atoms. The alkyl group of the solubilizing group may be substituted with one or more groups selected from methoxy, ethoxy, propoxy, hydroxy, and amino optionally substituted with one or two of methyl, ethyl and/or propyl, in particular methoxy, ethoxy or hydroxy, and/or one or more carbon atoms, in particular one, two, three or four carbon atoms, may be replaced by oxygen, sulfur or nitrogen. In certain embodiments, the solubilizing group is a linear C8-40 alkyl attached to the remaining part of the coupling reagent or ligand via an ether group and optionally substituted with a methoxy group at its terminal end. Suitable examples of the solubilizing group include 12-methoxy-n-dodecyloxy and n-dodecyloxy.

In further embodiments, the solubilizing group comprises a poly(alkylene glycol) group with 2 to 20 repeating units. The poly(alkylene glycol) in particular is a poly(ethylene glycole), poly(propylene glycol) or poly(butylene glycol), preferably a poly(ethylene glycole). The poly(alkylene glycol) group may have 2 to 15 repeating units, in particular 2 to 12 repeating units, 3 to 10 repeating units, 3 to 8 repeating units, or 4 to 6 repeating units, especially about 5 repeating units. The poly(alkylene glycol) group may be substituted with one or more groups selected from methyl, ethyl, propyl, methoxy, ethoxy, propoxy, hydroxy, and amino optionally substituted with one or two of methyl, ethyl and/or propyl, in particular methyl, ethyl or propyl. In certain embodiments, the poly(alkylene glycol) group is substituted at the terminal oxygen, in particular with methyl or ethyl. In further embodiments, the poly(alkylene glycol) group comprises the same substitution at each repeating unit, in particular a methyl or ethyl group. Suitable examples of the solubilizing group include poly(ethylene glycol) with 4 to 6 repeating units and optionally a methyl group at the terminal oxygen.

The one or more reactants in the reaction mixture may be any reactants suitable for performing the chemical reaction. The reactants in particular depend on the type of chemical reaction which is to be performed in the reaction mixture. In certain embodiments, the reaction mixture comprises one reactant, two reactants or three reactants. In specific embodiments, at least one of the reactants is not water-miscible or only partly water-miscible. A reactant which is only partly water-miscible in particular is only miscible with water at a concentration of 20 g/l or less, especially 10 g/l or less or 5 g/l or less, at room temperature. Exemplary reactants include boronic acids, boronate esters, organosilanes, halides, acids and/or corresponding activated esters, amines, alcohols and alkenes. In embodiments wherein the reaction mixture is for performing an amidation reaction, the reaction mixture in particular comprises one reactant being a carboxylic acid and one reactant being an amine, especially a primary amine.

The reactants can be used in any concentration which is feasible for performing the chemical reaction. In particular, the reactants are used at high concentrations. For example, the concentration of at least one of the reactants, especially of all reactants, in the reaction mixture is at least 0.1 M, in particular at least 0.5 M, at least 1.0 M, at least 1.1 M, at least 1.2 M, at least 1.3 M, at least 1.5 M, at least 1.7 M or at least 2.0 M. In certain embodiments wherein the reaction mixture additionally comprises an organic solvent, the concentration of one or more of the reactants in the reaction mixture is above the saturation concentration of its solubility or miscibility in the surfactant-water mixture. In particular, it is at least about 5%, especially at least about 10%, at least about 20%, at least about 30% or at least about 50% above said saturation concentration. In these embodiments, solubility or miscibility of the reactants is provided by the organic solvent in the reaction mixture. The person skilled in the art is able to select suitable reactants and their concentrations.

In certain embodiments, the reaction mixture may additionally comprise a base. The presence of the additional base in the reaction mixture in particular depends on the type of chemical reaction which is to be performed in the reaction mixture. The base may be an organic base or an inorganic base. In particular, the base is at least partly water-soluble or at least partly water-miscible. Exemplary bases include trialkylamines such as triethylamine (TEA), N-methylmorpholine (NMM), 1,8-diazabicyclo[5.4.0]undec-7-ene (DBU), 1,4-diazabicyclo[2.2.2]octane (DABCO), $K_3PO_4$, $NaHCO_3$ and $Na_2CO_3$. The concentration of the base in the reaction mixture in particular is in the range of 0.5 to 10 molar equivalents of one of the reactants, especially in the range of 0.9 to 6, 1.0 to 5, 1.2 to 4 or 1.5 to 3.5 molar equivalents of one of the reactants. If the reaction mixture is for performing a chemical reaction which does not need a base, the reaction mixture does not have to contain a base.

In specific embodiments, the reaction mixture further comprises an organic solvent. The organic solvent in the reaction mixture may be any organic solvent. Preferably, it shall not disturb or inhibit the chemical reaction and in particular shall increase the homogeneity of the reaction mixture. In certain embodiments, the organic solvent is water-miscible or partly water-miscible. The organic solvent especially is an aprotic organic solvent. Suitable examples of the organic solvent include acetone, tetrahydrofuran (THF) and derivatives thereof such as methyl tetrahydrofuran, pyridine, polyethylene glycol (PEG), polypropylene glycol (PPG), in particular PEG with an average molecular weight of about 100 g/mol to about 2000 g/mol such as PEG200, PEG600, PEG1000 and PEG2000, derivatives thereof such as mono- or dialkyl PEG, in particular mono- or dimethyl PEG, mono- or diethyl PEG and mono- or dipropyl PEG. Further examples include acetonitrile, dimethylformamide (DMF), dichloromethane (DCM), toluene, and alcohols such as a $C_{1-10}$ aliphatic alcohol, in particular 2-butyl alcohol. In certain embodiments, the organic solvent is not a base and/or does not act as base in the chemical reaction.

In specific embodiments, an organic solvent is used which increases the viscosity of the reaction mixture. For example, the viscosity of the reaction mixture containing the organic solvent is at least 1.25 cSt, especially at least 1.5 cSt, at least 1.75 cSt or at least 2.0 cSt. Suitable organic solvents which increase the viscosity of the reaction mixture include PEGs such as PEG200, PEG600 and PEG1000 (PEG with an average molecular weight of 200 g/mol, 600 g/mol and 1000 g/mol, respectively).

In specific embodiments, the reaction mixture comprises 0.1 to 50 volume equivalents of the organic solvent and 1 to 50 volume equivalents of the surfactant-water mixture per mass of the reactants or product, respectively. The amount of the organic solvent and the amount of the surfactant-water mixture are defined in relation to the amount of the theoretical product or alternatively the reactants of the chemical reaction. In case the amount is defined based on the theoretical product, 1 volume equivalent equals the total weight of the theoretical product obtained by 100% conversion in the chemical reaction. The weight of the theoretical product is converted into volume using a theoretical density of 1 g/ml. Hence, if for example 1.5 kg product is calculated based on 100% conversion, 1 volume equals 1.5 l. In case the amount is defined based on the reactants, 1 volume equivalent equals the total weight of the reactants. The weight of the reactants is converted into volume using a theoretical density of 1 g/ml. Hence, if for example 1.5 kg reactants are used in the reaction mixture, 1 volume equals 1.5 l.

In certain embodiments, the amount of the organic solvent in the reaction mixture is at least 0.2 volume equivalents, in particular at least 0.4 volume equivalents, at least 0.6 volume equivalents, at least 0.8 volume equivalents, at least 1.0 volume equivalent, at least 1.5 volume equivalents, or at least 2.0 volume equivalents. In further embodiments, the amount of the organic solvent in the reaction mixture is at most 40 volume equivalents, in particular at most 30 volume equivalents, at most 25 volume equivalents, at most 20 volume equivalents, at most 15 volume equivalents, at most 12 volume equivalents, or at most 10 volume equivalents. In specific embodiments, the amount of the organic solvent in the reaction mixture is in the range of 0.4 to 25 volume equivalents, in particular 0.8 to 15 volume equivalents. In certain embodiments, the amount of the organic solvent in the reaction mixture is in the range of from 1% to 70%, in particular from 2% to 65%, from 3% to 60%, from 4% to 55% or from 5% to 50%.

In certain embodiments, the amount of the surfactant-water mixture in the reaction mixture is at least 1.5 volume equivalents, in particular at least 2.0 volume equivalents, at least 2.5 volume equivalents, at least 3.0 volume equivalents, at least 3.5 volume equivalents, at least 4.0 volume equivalents, or at least 5.0 volume equivalents. In further embodiments, the amount of the surfactant-water mixture in the reaction mixture is at most 45 volume equivalents, in particular at most 40 volume equivalents, at most 35 volume equivalents, at most 30 volume equivalents, at most 25 volume equivalents, at most 22 volume equivalents, or at most 20 volume equivalents. In specific embodiments, the amount of the surfactant-water mixture in the reaction mixture is in the range of 1.5 to 25 volume equivalents, in particular 2.0 to 20 volume equivalents. In certain embodiments, the amount of the surfactant-water mixture in the reaction mixture is in the range of from 30% to 98%, in particular from 35% to 95%, from 40% to 92%, from 45% to 90% or from 50% to 85%.

The amount of organic solvent and surfactant-water mixture together in particular may in certain embodiments not exceed 30 volumes, especially it is 25 volume equivalents or less, 20 volume equivalents or less or even 15 volume equivalents or less. In specific embodiments, the volume of the organic solvent in the reaction mixture is in the range of about 1% to about 200% of the volume of the surfactant-water mixture, in particular in the range of about 2% to about 150%, about 3% to about 120%, about 4% to about 110% or about 5% to about 100%.

In one embodiment, the reaction mixture is of industrial scale. It may for example have a volume of at least 1 l, in particular at least 10 l, at least 100 l, or at least 1000 l. In another embodiment, the reaction mixture is of microscale. It may for example have a volume of 10 ml or less, in particular 1 ml or less, 100 µl or less, 10 µl or less or 1 µl or less.

The reaction mixture is a charge or batch mixture for performing a chemical reaction. In certain embodiments the reaction mixture does not comprise any products of the reaction or comprises only residual amount of any products of the reaction. In other embodiments, it may also contain a significant amount of the product of the chemical reaction. In further embodiments, the reaction mixture does not comprise all reactants necessary to perform the chemical reaction. In particular, the reaction mixture comprises only one reactant. For example, in these embodiments one reactant may be added slowly to the reaction mixture and is directly consumed by the chemical reaction. In certain embodiments, the reaction mixture is a homogeneous mixture, especially a colloidal suspension. In particular, the reaction mixture does not contain aggregated or oiled out components such as reactant or product.

In a second aspect, the present invention provides a method of performing a chemical reaction, comprising the steps of
 (a) providing a reaction mixture as described herein, and
 (b) allowing the chemical reaction to proceed.

The reaction mixture especially comprises one or more reactants, a catalyst, and a surfactant-water mixture, wherein the catalyst is (a) a coupling reagent comprising one or more solubilizing groups; or (b) a metal ion in complex with a ligand comprising one or more solubilizing groups; wherein the solubilizing group comprises a C5-50 alkyl group or a poly(alkylene glycol) group with 2 to 20 repeating units. The reaction mixture in particular may exhibit any of the features, embodiments and examples described herein including combinations thereof.

The chemical reaction may be any chemical reactions which can be performed in a medium comprising a surfactant-water mixture. In particular organic chemical synthesis reactions can be performed, for example with at least partly hydrophobic compounds. Exemplary chemical reactions include chemical reactions selected from the group consisting of cross-coupling reactions such as Suzuki cross-coupling, Suzuki-Miyaura cross-coupling, Sonogashira cross-coupling, Heck cross-coupling, Buchwald-Hartwig cross-coupling, Negishi cross-coupling, Stille cross-coupling, Miyaura borylation, Hiyama cross-couplings, and olefin metathesis; copper-mediated cross-couplings, nickel-mediated cross-couplings, nucleophilic substitutions ($S_N2$) such as nucleophilic aromatic substitution ($S_NAr$); amidation; oxidation; reduction such as reduction of nitro groups, oxime groups, azide groups, nitrile groups and amide groups; hydrogenation and debenzylation. In certain embodiments, the chemical reaction is an amidation reaction. The reactants and the catalyst present in the reaction mixture are suitable for the specific chemical reaction. In particular, the reactants and the catalyst are specifically chosen so that the chemical reaction proceeds as desired.

In certain embodiments, the chemical reaction is allowed to proceed in step (b) at reaction conditions suitable for performing the chemical reaction. In particular, the reaction conditions include a temperature of 90° C. or less, especially 80° C. or less, 70° C. or less, 60° C. or less, 50° C. or less, 40° C. or less or 30° C. or less. For example, the chemical reaction may be allowed to proceed at about room temperature. In specific embodiments, the reaction mixture is agitated, in particular stirred, during the course of the chemical reaction.

For some chemical reactions, the order and speed of the addition of the various components of the reaction mixture is important. In some embodiments, one or more of the reactants are added slowly to the surfactant-water mixture, optionally comprising further components of the reaction mixture such as other reactants, the catalyst and the base. This in particular applies to reactants which have a low solubility in water. Slow addition in this respect refers for example to the addition of the reactant over a time period of at least 5 min, in particular at least 7 min, at least 10 min, at least 15 min, at least 20 min, at least 30 min, at least 45 min or at least 60 min. A low solubility in water in particular refers to a water solubility of 20 g/l or less, especially 10 g/l or less or 5 g/l or less at room temperature. In these embodiments, an organic solvent may be added to the surfactant-water mixture before addition of the reactant or it may be added together with the reactant. For example, the reactant may be mixed with or solved in an organic solvent and then added to the surfactant-water mixture.

The methods of performing a chemical reaction may comprise the further step of isolating the product of the chemical reaction. In particular, this step is performed after completion of the chemical reaction. The product is in particular separated from one or more, in particular essentially all of the other components of the reaction mixture. For example, the product is separated from one or more of remaining reactants, side products, catalysts, bases, organic solvents and/or surfactant-water mixture. Isolation of the product may be achieved by means and techniques known in the art, including for example evaporation of solvents, aggregation or crystallization and filtration, phase separation, chromatographic separation and others.

In certain embodiments, the reaction mixture is a homogeneous mixture throughout the entire chemical reaction, especially a colloidal suspension. "Throughout the entire chemical reaction" in this respect in particular means from the establishment of the final reaction mixture until the completion or termination of the chemical reaction.

The present invention improves the solubility of the reactants and products in the surfactant-water mixture and provides a stable and homogeneous reaction mixture. Thereby, the yield of the chemical reaction is increased and the amount of unwanted side products obtained by the chemical reaction is reduced. In view of this, the present invention in a further aspect provides a method of increasing the yield of a chemical reaction performed in a surfactant-water mixture, comprising the steps of (a) providing a reaction mixture comprising one or more reactants, a catalyst, and a surfactant-water mixture, wherein the catalyst is a coupling reagent comprising one or more solubilizing groups, or a metal ion in complex with a ligand comprising one or more solubilizing groups; wherein the solubilizing group comprises a $C_{5-50}$ alkyl group or a poly(alkylene glycol) group with 2 to 20 repeating units; and (b) allowing the chemical reaction to proceed.

In a further aspect, the present invention provides a method of decreasing the amount of side products produced in a chemical reaction performed in a surfactant-water mixture, comprising the steps of (a) providing a reaction mixture comprising one or more reactants, a catalyst, and a surfactant-water mixture, wherein the catalyst is a coupling reagent comprising one or more solubilizing groups, or a metal ion in complex with a ligand comprising one or more solubilizing groups; wherein the solubilizing group comprises a $C_{5-50}$ alkyl group or a poly(alkylene glycol) group with 2 to 20 repeating units; and (b) allowing the chemical reaction to proceed.

The embodiments, features and examples described herein, including combinations thereof, for methods of performing a chemical reaction and reaction mixtures likewise apply to the method of increasing the yield of, and the method of decreasing the amount of side products produced in a chemical reaction performed in a surfactant-water mixture and the reaction mixture provided in step (a) thereof, respectively.

The reaction mixture may be provided in step (a) by adding the different components to each other in any suitable order. For example, providing the reaction mixture in step (a) may include providing a surfactant-water mixture and adding to said surfactant-water mixture a catalyst and one or more reactants.

The present invention also provides the use of a catalyst being (a) a coupling reagent comprising one or more solubilizing groups; or (b) a metal ion in complex with a ligand comprising one or more solubilizing groups;

wherein the solubilizing group comprises a $C_{5-50}$ alkyl group or a poly(alkylene glycol) group with 2 to 20 repeating units;

for increasing the yield of, and/or decreasing the amount of side products produced in a chemical reaction performed in a surfactant-water mixture.

The expression "comprise", as used herein, besides its literal meaning also includes and specifically refers to the expressions "consist essentially of" and "consist of". Thus, the expression "comprise" refers to embodiments wherein the subject-matter which "comprises" specifically listed elements may and/or indeed does encompass further elements as well as embodiments wherein the subject-matter which "comprises" specifically listed elements does not comprise further elements. Likewise, the expression "have" is to be understood as the expression "comprise", also including and specifically referring to the expressions "consist essentially of" and "consist of".

Numeric ranges described herein are inclusive of the numbers defining the range. The headings provided herein are not limitations of the various aspects or embodiments of this invention which can be read by reference to the specification as a whole. According to one embodiment, subject matter described herein as comprising certain steps in the case of methods or as comprising certain ingredients in the case of compositions refers to subject matter consisting of the respective steps or ingredients. It is preferred to select and combine specific aspects and embodiments described herein and the specific subject-matter arising from a respective combination of specific embodiments also belongs to the present disclosure.

FIGURES

FIG. 1 shows the chemoselective conversion of 4-bromobenzoic acid with 0.5 eq 3-methylphenol and 0.5 eq 3-ethylaniline using triazine 6c (A) or 6h (B) as coupling reagent in TPGS-750-M in water (2 wt %). In (A) the overall conversion (triangles) and the conversions into the amide (diamond) and the ester (circle) is shown. In (B) no conversion into the ester was observed, so that the conversion into the amide is identical to the overall conversion.

EXAMPLES

To a mixture of carboxylic acid (1 eq), NaHCO$_3$, (1 eq), and amine (1.1 eq) in TPGS-750-M (2% in water, 10 eq V) was added triazine (1.1 eq) in solution in a water-miscible co-solvent (1 eq V). The reaction was allowed to stir at 25° C. until completion (typically 2 to 5 hours). At completion, the product was either precipitated by the addition of more water, or extracted in isopropyl acetate, and filtered through a short plug of silica to provide the desired amide product.

A variety of derivatized triazines (6b to 6h) were compared with the reference one (6a) on the following challenging model transformation:

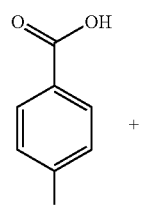

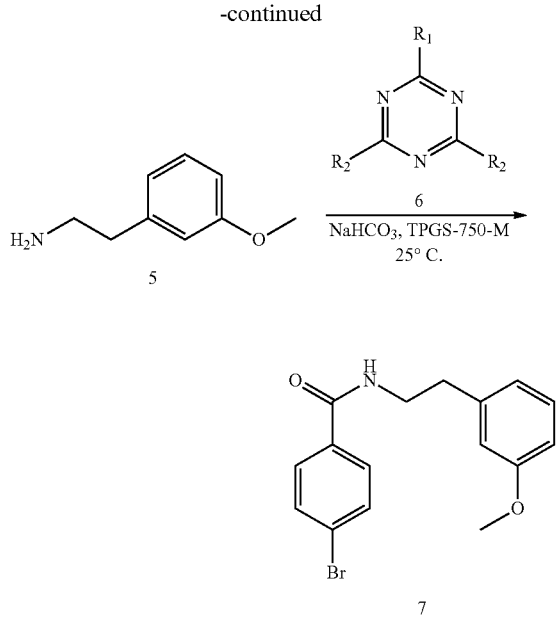

The following triazine derivatives were evaluated, giving the indicated conversion ratio:

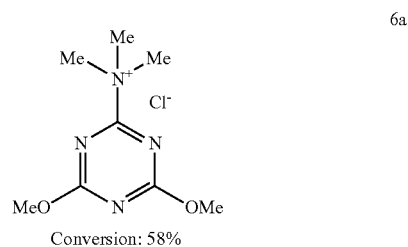

Conversion: 58%

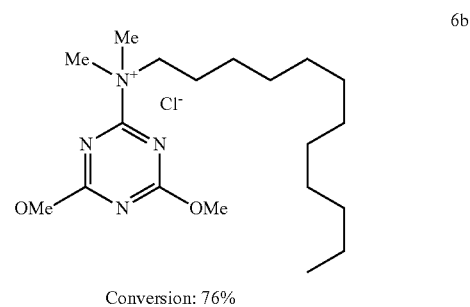

Conversion: 76%

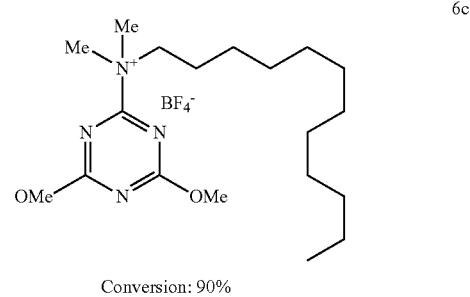

Conversion: 90%

-continued

6d
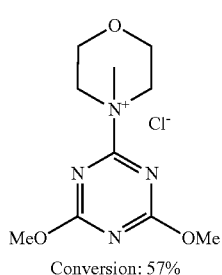
Conversion: 57%

6e
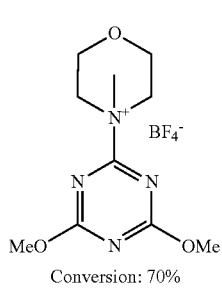
Conversion: 70%

6f
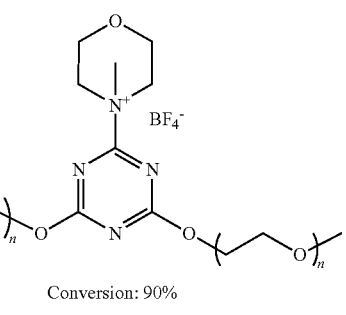
Conversion: 90%

6g
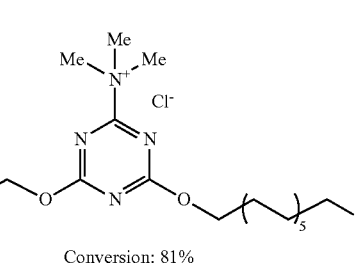
Conversion: 81%

6h
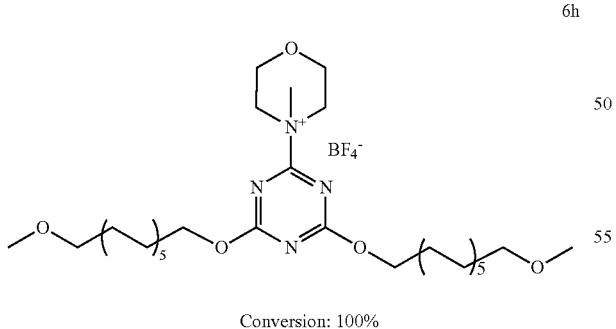
Conversion: 100%

The conversions were monitored as a direct indicator of the yield (no competitive side-reaction). This demonstrated that tailoring the reagent for the medium had a profound impact on its outcome.

Amidation was then performed with different amines and carboxylic acids using the coupling reagent 6c or 6h, respectively. Conversion ratios were as follows:

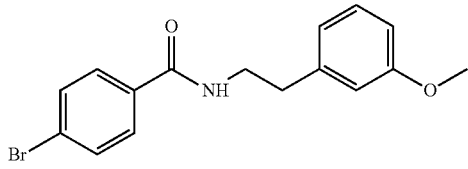
6c: 90%
6h: 100%

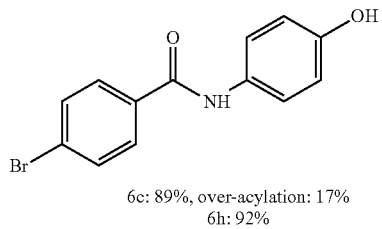
6c: 89%, over-acylation: 17%
6h: 92%

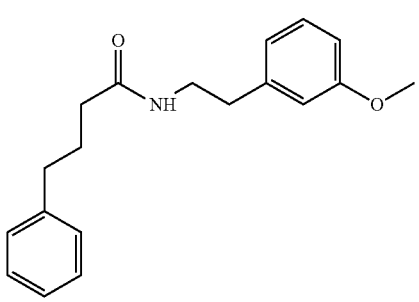
6c: 90%
6h: 88%

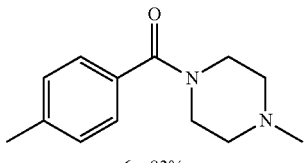
6c: 83%
6h: 88%

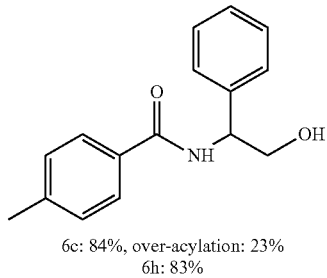
6c: 84%, over-acylation: 23%
6h: 83%

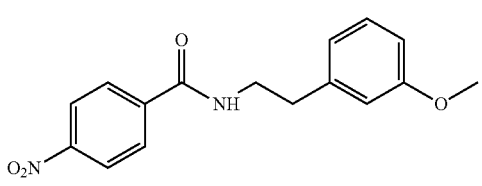
6c: 72%
6h: 92%

-continued

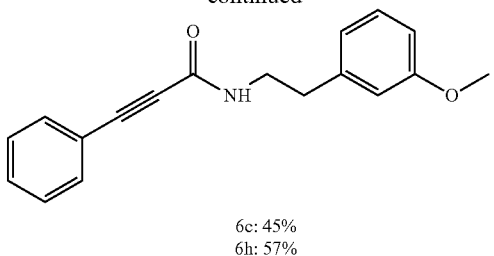

6c: 45%
6h: 57%

We demonstrated here that the non-participating side-chains had the most profound impact, and always showed as good or better selectivity and yield.

Another and even more spectacular feature is the selectivity that ensues. On the highly demanding reaction below, triazine 6c or 6h, respectively, was used as coupling reagent and the formation of amide and ester was monitored.

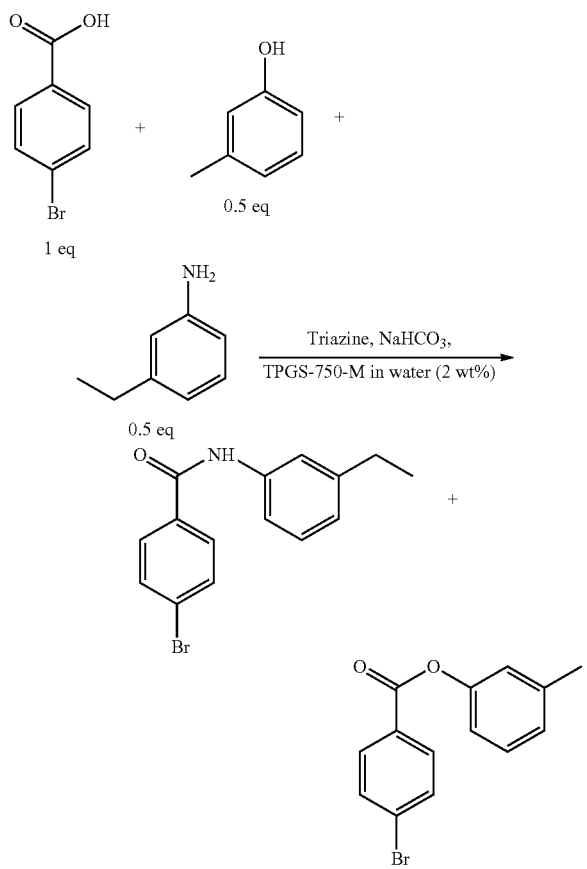

The results are shown in FIG. 1. As can be seen, saw almost perfect selectivity was obtained in the case of triazine 6h (FIG. 1B). This is all the more remarkable as it is almost impossible to obtain with any other conditions. Also with triazine 6c, only a very small amount of ester was obtained (FIG. 1A).

The invention claimed is:

1. A reaction mixture comprising one or more reactants, a catalyst and a surfactant-water mixture, wherein the catalyst is
   a coupling reagent, wherein the coupling reagent is a 1,3,5-triazine comprising one or more solubilizing groups;
   wherein the solubilizing group comprises a $C_{5-50}$ alkyl group or a poly(alkylene glycol) group with 2 to 20 repeating units,
   wherein the surfactant-water mixture comprises a surfactant and water, and the surfactant is DL-α-Tocopherol methoxypolyethylene glycol succinate.

2. The reaction mixture according to claim 1, wherein the solubilizing group comprises a $C_{5-50}$ alkyl group and has one or more of the following features:
   (i) the $C_{5-50}$ alkyl group is linear;
   (ii) the $C_{5-50}$ alkyl group comprises 8-15 carbon atoms;
   (iii) being substituted with one or more groups selected from methoxy, ethoxy, propoxy, hydroxy, amino optionally substituted with one or two of methyl, ethyl and propyl; and
   (iv) 12-methoxydodecyl or dodecyl.

3. The reaction mixture according to claim 1, wherein the solubilizing group comprises a poly(alkylene glycol) group with 2 to 20 repeating units, further wherein the poly(alkylene glycol) group has one or more of the following features:
   (i) the poly(alkylene glycol) group is a poly(ethylene glycol) group or poly(propylene glycol) group;
   (ii) the poly(alkylene glycol) group has 3 to 8 repeating units;
   (iii) being substituted with one or more groups selected from methyl, ethyl, propyl, methoxy, ethoxy, propoxy, hydroxy, and amino optionally substituted with one or two of methyl, ethyl and propyl; and
   (iv) a poly(ethylene glycol) group with 4 to 6 repeating units, optionally substituted with methyl or ethyl at a terminal oxygen.

4. The reaction mixture according to claim 3, wherein the 1,3,5-triazine has one or more of the following features:
   (i) comprising a quaternary amino group, wherein the quaternary amino group is attached to a 2-position of a triazine ring;
   (ii) being substituted with at least one of methyl, ethyl, propyl, methoxy, ethoxy and propoxy at least one of a 4- and a 6-position of the triazine ring;
   (iii) the one or more solubilizing groups being attached to at least one of the quaternary amino group, the 4- and 6-position of the triazine ring.

5. The reaction mixture according to claim 4, wherein the quaternary amino group is a trimethylamino or an N-methyl-N-morpholino group.

6. The reaction mixture according to claim 1, wherein the solubilizing group is attached to a remaining part of the coupling reagent or ligand via an ether, amine, ester or amide bond.

7. The reaction mixture according to claim 1, wherein the coupling reagent or ligand comprises one or two solubilizing groups.

8. The reaction mixture according to claim 1, wherein the concentration of the surfactant in the surfactant-water mixture is 0.5 to 5% (w/w).

9. The reaction mixture according to claim 1, wherein the reaction mixture comprising one reactant or two reactants.

10. The reaction mixture according to claim 1, further comprising an organic solvent.

11. The reaction mixture according to claim 1, wherein the reaction mixture is a homogeneous mixture.

12. The reaction mixture according to claim 1, wherein the reaction mixture is a colloidal suspension.

13. A method of performing a chemical reaction, comprising the steps of
(a) providing a reaction mixture according to claim 1, and
(b) allowing the chemical reaction to proceed.

14. The method according to claim 13, further comprising the step of isolating the product of the chemical reaction.

15. The method according to claim 13, wherein the reaction mixture is a homogeneous mixture throughout the entire chemical reaction.

16. The method according to claim 13, wherein the reaction mixture is a colloidal suspension throughout the entire chemical reaction.

17. A method of increasing a yield of a chemical reaction performed in a surfactant-water mixture, comprising the steps of
(a) providing a reaction mixture comprising one or more reactants, a catalyst, and a surfactant-water mixture, wherein the catalyst is
a coupling reagent, wherein the coupling reagent is a 1,3,5-triazine comprising one or more solubilizing groups,
wherein the solubilizing group comprises a $C_{5-50}$ alkyl group or a poly(alkylene glycol) group with 2 to 20 repeating units,
wherein the surfactant-water mixture comprises a surfactant and water, and the surfactant is DL-α-Tocopherol methoxypolyethylene glycol succinate; and
(b) allowing the chemical reaction to proceed.

18. A method of decreasing an amount of side products produced in a chemical reaction performed in a surfactant-water mixture, comprising the steps of
(a) providing a reaction mixture comprising one or more reactants, a catalyst, and a surfactant-water mixture, wherein the catalyst is
a coupling reagent, wherein the coupling reagent is a 1,3,5-triazine comprising one or more solubilizing groups;
wherein the solubilizing group comprises a $C_{5-50}$ alkyl group or a poly(alkylene glycol) group with 2 to 20 repeating units,
wherein the surfactant-water mixture comprises a surfactant and water, and the surfactant is DL-α-Tocopherol methoxypolyethylene glycol succinate; and
(b) allowing the chemical reaction to proceed.

* * * * *